United States Patent
Kahlman et al.

(10) Patent No.: US 9,778,187 B2
(45) Date of Patent: Oct. 3, 2017

(54) CORRECTION FOR OSMOTIC PRESSURE VARIATIONS IN CHEMO-OPTICAL SENSOR SPOTS

(71) Applicant: KONINKLIJKE PHILIPS N.V., Eindhoven (NL)

(72) Inventors: Josephus Arnoldus Henricus Maria Kahlman, Tilburg (NL); Nicolaas Lambert, Waalre (NL); Hans Willem Van Kesteren, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1 day.

(21) Appl. No.: 14/893,961

(22) PCT Filed: May 30, 2014

(86) PCT No.: PCT/EP2014/061244
§ 371 (c)(1),
(2) Date: Nov. 25, 2015

(87) PCT Pub. No.: WO2014/195236
PCT Pub. Date: Dec. 11, 2014

(65) Prior Publication Data
US 2016/0116408 A1  Apr. 28, 2016

(30) Foreign Application Priority Data
Jun. 6, 2013 (EP) .................................. 13170726

(51) Int. Cl.
*G01N 21/64* (2006.01)
*G01N 33/497* (2006.01)
*G01N 33/84* (2006.01)
*A61B 5/1468* (2006.01)
*G01N 21/77* (2006.01)

(52) U.S. Cl.
CPC ....... *G01N 21/6408* (2013.01); *A61B 5/1468* (2013.01); *G01N 21/6428* (2013.01); *G01N 21/77* (2013.01); *G01N 33/497* (2013.01); *G01N 33/84* (2013.01); *G01N 2021/6439* (2013.01); *G01N 2021/6441* (2013.01); *G01N 2021/775* (2013.01); *G01N 2021/7786* (2013.01); *G01N 2201/062* (2013.01); *G01N 2201/13* (2013.01)

(58) Field of Classification Search
CPC ................ A61B 5/1455; A61B 5/1468; G01N 2021/6439; G01N 2021/6441; G01N 2021/775; G01N 2021/7786; G01N 21/6408; G01N 21/6428; G01N 21/77; G01N 2201/062; G01N 2201/13; G01N 33/4925; G01N 33/497; G01N 33/84; Y10T 436/25875

USPC .......... 436/34, 68, 164, 167, 169, 172, 181; 422/420, 82.05, 82.08, 83, 88; 702/22, 702/23, 24, 32; 250/252.1, 459.1, 573

See application file for complete search history.

(56) References Cited

U.S. PATENT DOCUMENTS

| | | | |
|---|---|---|---|
| 5,102,625 A | 4/1992 | Milo | |
| 5,462,880 A * | 10/1995 | Kane | .................. G01N 21/643 422/82.07 |
| 6,602,716 B1 | 8/2003 | Klimant | |
| 2002/0187515 A1 | 12/2002 | Chee et al. | |
| 2006/0257094 A1* | 11/2006 | McEvoy | .............. G01N 21/643 385/147 |
| 2009/0004751 A1 | 1/2009 | Leiner et al. | |
| 2016/0007894 A1* | 1/2016 | Kahlman | ............. A61B 5/6833 600/323 |
| 2016/0135723 A1* | 5/2016 | Kahlman | ........... A61B 5/14552 600/323 |

FOREIGN PATENT DOCUMENTS

| | | |
|---|---|---|
| EP | 1943499 A2 | 7/2008 |
| WO | 02056023 A1 | 7/2002 |
| WO | 2007050539 A2 | 5/2007 |

OTHER PUBLICATIONS

Borisov et al. Applied Spectroscopy, vol. 60, No. 10, 2006, pp. 1167-1173.*
Kocincova, "New pH Sensitive Sensor Materials. Luminescent Fiber-Optic Dual Sensors for Non-Invasive and Simultandous Measurement of pH and pO2 (Dissolved Oxygen) in Biological Systems", PhD Thesis, University of Regensburg, 2007, pp. 1-150.
Schaferling, "The Art of Fluorescence Imaging With Chemical Sensors" Chemical Sensors, Angewandte Chemie International Edition, 51(15), 2012, pp. 3532-3554.
Liebsch et al, "Fluorescent Imaging of pH With Optical Sensors Using Time Domain Dual Lifetime Referencing", Analytical Chemistry, American Chemical Society, vol. 73, No. 17, pp. 4354-4363, 2001.

* cited by examiner

*Primary Examiner* — Maureen Wallenhorst
(74) *Attorney, Agent, or Firm* — Michael W. Haas

(57) ABSTRACT

The present invention relates to a method for optically determining the concentration of a gas. The method includes using at least two luminescent dyes, the first being insensitive to the concentration of a gas with respect to the luminescence response (reference dye) and the second being sensitive to the concentration of a gas with respect to the luminescence response (indicator dye) the dyes show different luminescence decay times so that the resultant phase angle is indicative for the concentration of a gas, wherein the detected luminescent amplitude of the reference dye at a first moment in time is utilized to correct for sensitivity changes after the first moment.

15 Claims, 10 Drawing Sheets

CORRECTION FOR OSMOTIC PRESSURE VARIATIONS IN CHEMO-OPTICAL SENSOR SPOTS

CROSS-REFERENCE TO PRIOR APPLICATIONS

This application is the U.S. National Phase application under 35 U.S.C. §371 of International Application Serial No. PCT/EP2014/061244, filed on May 30, 2014, which claims the benefit of European Patent Application Serial No. 13170726.7, filed on Jun. 6, 2013. These applications are hereby incorporated by reference herein.

FIELD OF THE INVENTION

The present invention relates to a method for optically determining the concentration of a gas, using at least two luminescent dyes, the first being in-sensitive to the concentration of a gas with respect to the luminescence response (reference dye) and the second being sensitive to the concentration of a gas with respect to the luminescence response (indicator dye), wherein said dyes show different luminescence decay times so that the resultant phase angle is indicative for the concentration of a gas, characterized in that the detected luminescent amplitude of the reference dye at a first moment in time is utilized to correct for sensitivity changes after said moment. The present invention also relates to a corresponding method for quality assessment of the measurement of an optical sensor for determining the concentration of a gas.

BACKGROUND OF THE INVENTION

Neuromuscular disease, chronic obstructive pulmonary disease (COPD) and obese hypoventilation patients often suffer from chronic respiratory failure. Said patients need regular treatment of their respiratory failure at home. Hypoxemic patients are treated by oxygen therapy (mostly without ventilator support), while treatment by Invasive Ventilation (IV) and Non Invasive Ventilation (NIV) with environmental air helps bringing the high carbon dioxide ($CO_2$) blood gas level of hypercapnic patients back to an acceptable level. The efficacy of the ventilation is checked by measuring the base-line and the trends in the arterial oxygen and carbon dioxide levels during nocturnal NIV.

Arterial blood gas measurements form the golden standard. Before starting ventilation treatment at home, patients stay at the hospital to optimize ventilator settings and monitor arterial blood gas values. Depending on disease severity and stability, patients have to return more or less regularly to the hospital for checks. A respiratory nurse can also visit the patient at home to check the ventilator and to install equipment that enables non-invasive monitoring of blood gas partial pressures. At home, blood gas levels are monitored typically during a night and data are stored together with ventilator and respiratory data for later analysis at the hospital.

The state of the art in non-invasive blood oxygenation monitoring, is by measuring the arterial oxygen saturation, which relates to the partial oxygen pressure via the oxygen dissociation curve. Pulse oximetry ($SpO_2$) is an optical method for non-invasive monitoring of arterial oxygen saturation in a patient and has become one of the most commonly used technologies in clinical practice. Pulse oximetry is a reasonably low cost technology and is easy to use. It is the preferred method for blood oxygenation monitoring at home.

The state of the art in non-invasive monitoring of the partial pressure of $CO_2$ is by means of capnography or by transcutaneous $CO_2$ ($PtcCO_2$) monitoring. For intubated patients with a healthy lung the end tidal $CO_2$ ($etCO_2$) value obtained by capnography offers a good indication of the arterial $CO_2$ value. However, in case of non-invasive ventilation where air leaks between mask and face are usually present and the patients have severe respiratory diseases capnography is often not a reliable method. In most hospitals a combination is used of capnography for trend monitoring and analysis of an arterial blood sample to obtain an occasional accurate value.

Transcutaneous $CO_2$ monitoring is not disrupted by air-leaks and respiratory diseases but requires trained personal to obtain reliable values and shows some inaccuracy due to variation in skin properties among adults. At home $CO_2$ blood gas monitoring is less frequently used than oximetry despite its high relevance for patients receiving ventilation.

Current transcutaneous $CO_2$ sensors are all based on a 40 year old concept of (i) a thermostatically controlled heater to increase blood perfusion and gas-permeability of the skin; (ii) a fluid layer between skin and sensor membrane; (iii) a gas-permeable membrane covering the sensor; (iv) an electrolyte solution between membrane and sensor; (v) a sensor comprising an electrochemical pH sensor and reference electrode; and (v) an algorithm to compensate for temperature effects and skin metabolism.

U.S. Pat. No. 6,602,716 B1 describes a method and device for fluorimetric determination of a biological, chemical or physical parameter, in particular gaseous $CO_2$ or $NH_3$, of a sample utilizing two different luminescent materials, the first being sensitive to the parameter, at least with respect to the luminescence intensity, the second being insensitive to the parameter, at least with respect to luminescence intensity and decay times. The application further indicates that phase modulation techniques can be employed to determine the mean phase shift of the luminescence signal. The phase angle $\phi_m$ thus depends on the ratio of the two signal intensities but not on the absolute signal level and will permit the referencing of the intensity of the short-lived indicator dye component.

A further example of a prior art chemo-optical sensor for transcutaneous application is depicted in FIG. 1, wherein on top of an optical transparent carrier material two layers of "silicon rubber-like" gas-permeable materials are deposited The first layer—the sensing layer—comprises a mixture of two luminescent dyes in a lipophilic phase transfer agent within a hydrophobic polymer, namely a reference dye having a long luminescent life-time and a pH-sensitive indicator dye having a short luminescent life-time. A second membrane layer comprises light reflecting material ($TiO_2$) particles and prevents ion transport to and from the sensing layer. $CO_2$ gas typically diffuses through said membrane into the first (sensing) layer and changes the pH, which in turn modifies the fluorescence from the indicator dye. By using a dual life-time referencing technique, which effectively measures the time response of modulated light excitation, the percentage of $CO_2$ gas can be calculated.

The lipophilic phase transfer agent also serves as chemical buffer material to provide water for the production of carbonic acid. However, osmotic imbalance at the site of application of the sensor may initiate, for example, water transport in the sensor, which could lead to unwanted sensitivity changes of the sensor. Typically, such changes require a complete and time-consuming re-calibration of the sensor.

In consequence, there is a need for the development of a methodology allowing to compensate induced gas concentration measurement inaccuracy, in particular without the need of additional re-calibration of the chemo-optical sensor.

OBJECTS AND SUMMARY OF THE INVENTION

The present invention addresses these needs and provides methods for detecting inaccuracy of the optically determined concentration of a gas and for correcting such inaccuracy. The above objective is specifically accomplished by a method for optically determining the concentration of a gas, using at least two luminescent dyes, the first being insensitive to the concentration of a gas with respect to the luminescence response (reference dye) and the second being sensitive to the concentration of a gas with respect to the luminescence response (indicator dye), wherein said dyes show different luminescence decay times so that the resultant phase angle is indicative for the concentration of a gas, characterized in that the detected luminescent amplitude of the reference dye at a first moment in time is utilized to correct for sensitivity changes after said moment. In particular, it was surprisingly found by the inventors that the reference dye in a chemo-optical sensor unit, which could experimentally be proven to be insensitive for $O_2$, $CO_2$ and ions, may function as clear indicator for the sensitivity of the indicator layer. The sensitivity may, for example, be influenced by environmental osmolarity, e.g. at a transcutaneous application site of a chemo-optical sensor unit. This may lead, inter alia, to changes in the water content of the indicator layer. On the basis of this surprising finding measurements of the reference dye may be used to correct obtained measurement data of chemo-optical sensor units irrespective of the osmotic situation in situ since any water transport activity or water accumulation or efflux in the sensing layer of a sensor unit is detectible via the indicator function of the reference dye for water content. This allows to use a chemo-optical sensor unit in different osmotic environments, which may be unbalanced with respect to the initial state of the chemo-optical sensor unit without the need to recalibrate the chemo-optical sensor unit. Accordingly, the concentration of gases such as $O_2$ and in particular $CO_2$ may effectively be determined by the chemo-optical sensor unit without the need for any additional calibration step and without fearing a progressive falsification or invalidity of the measured values due to an influence of water influx to the sensing layer. Thus, potential osmolality changes in the sensing structures of a chemo-optical sensor may effectively be compensated by vector-decomposition on the basis of the reference dye signal.

In a preferred embodiment, said luminescent dyes are excited by a single light source.

In a further preferred embodiment, said luminescent dyes are excited simultaneously.

In another preferred embodiment of the present invention said luminescent dyes are provided in a sensing layer of a chemo-optical sensor unit.

In a further preferred embodiment said chemo-optical sensor unit comprises, adjacent to said sensing layer, at least one gas-permeable layer, adapted to pass gas whose concentration is to be measured through the gas-permeable layer towards the sensing layer.

In an additional embodiment, said gas-permeable layer is adapted to prevent light from passing through the gas-permeable layer.

In yet another preferred embodiment, said optical sensor is adapted to operate with a contact medium interposed at least between the gas-permeable layer and the surface layer on which the optical sensor is to be applied.

In a particularly preferred embodiment of the present invention, the method comprises measuring the phase behavior of luminescent responses of said reference and indicator dyes by a single detector, and obtaining a luminescent response vector $\vec{F}$ being independent of the total intensity of both luminescent dyes by the phase behavior measured, further de-composing the measured luminescent response vector $\vec{F}$ into an imaginary part ($\beta$) reflecting solely the said reference dye and a real part ($\alpha$) being a summation of the real part of the reference dye and of the indicator dye according to the formula (I)

$$\vec{F}=A\,e^{i\phi}=Re(\vec{F})+i\,Im(\vec{F})=A\cos(\omega t)+i\,A\sin(\omega t)=\alpha+i\beta$$

wherein $\alpha$ and $\beta$ are both time variant, and compensating the measured luminescent response after a first moment in time on the basis of the reference dye according to the formula (II)

$$\alpha' = \frac{\alpha}{1+k\partial(t)}$$

wherein (III)

$$\partial(t) = \frac{\beta(t)-\beta(0)}{\beta(0)}$$

and wherein k is a constant reflecting the ratio of sensitivity for osmolarity of said luminescent dyes, and determining the concentration of a gas via the phase angle $\phi$ of the resultant luminescent response vector $\vec{F}$ (IV)

$$\vec{F}=\alpha'+i\beta.$$

Preferably the constant k is a non-linear function of reference dye intensity.

In a specific embodiment of the present invention, said imaginary part ($\beta$) and said real part ($\alpha$) of the measured luminescence response are low pass filtered.

In a further embodiment of the method as described above, the steady state ratio between the luminescence of said reference dye and of said indicator dye in one osmotic environment is used as calibrator for one or more different osmotic environments.

In yet another preferred embodiment of the method as described above, the dynamics of the steady state ratio between the luminescence of said reference dye and of said indicator dye in one osmotic environment is used as calibrator for the dynamics of changing osmotic environments.

In a further aspect the present invention relates to a method for quality assessment of the measurement of an optical sensor for determining the concentration of a gas, using at least two luminescent dyes, the first being insensitive to the concentration of a gas with respect to the luminescence response (reference dye) and the second being sensitive to the concentration of a gas with respect to the luminescence response (indicator dye), wherein said dyes show different luminescence decay times so that the resultant phase angle is indicative for the concentration of a gas, characterized in that the detected luminescent amplitude of the reference dye at a first moment in time indicates sensitivity changes after said moment, the quality assessment comprising the determination of an imaginary part ($\beta$) according to formula (I)

$$\vec{F} = A\, e^{i\phi} = Re(\vec{F}) + i\, Im(\vec{F}) = A\cos(\omega t) + i\, A\sin(\omega t) = \alpha + i\beta$$

wherein a real part ($\alpha$) is a summation of the real part of the reference dye and of the indicator dye and wherein a slow and/or gradual variation of the imaginary part ($\beta$) is indicative of an acceptable measurement quality and wherein a fast changing or fluctuating variation of said imaginary part ($\beta$) is indicative of a non-acceptable measurement quality.

In a preferred embodiment of all methods described above, said gas concentration is blood gas concentration. It is particularly preferred that gas concentrations of $O_2$ and/or $CO_2$, more preferably gas concentration of $CO_2$ are determined.

In a further preferred embodiment all methods described above, said sensitivity changes take place in an osmotically unbalanced environment such as a body surface. In a particularly preferred embodiment, said sensitivity changes take place on or in the human or animal skin.

In a particularly preferred embodiment of the present invention, said determination of the concentration of a gas as mentioned herein above is a transcutaneous determination of the concentration of $CO_2$ at or in the human skin.

DETAILED DESCRIPTION OF THE EMBODIMENTS

Figure 1:
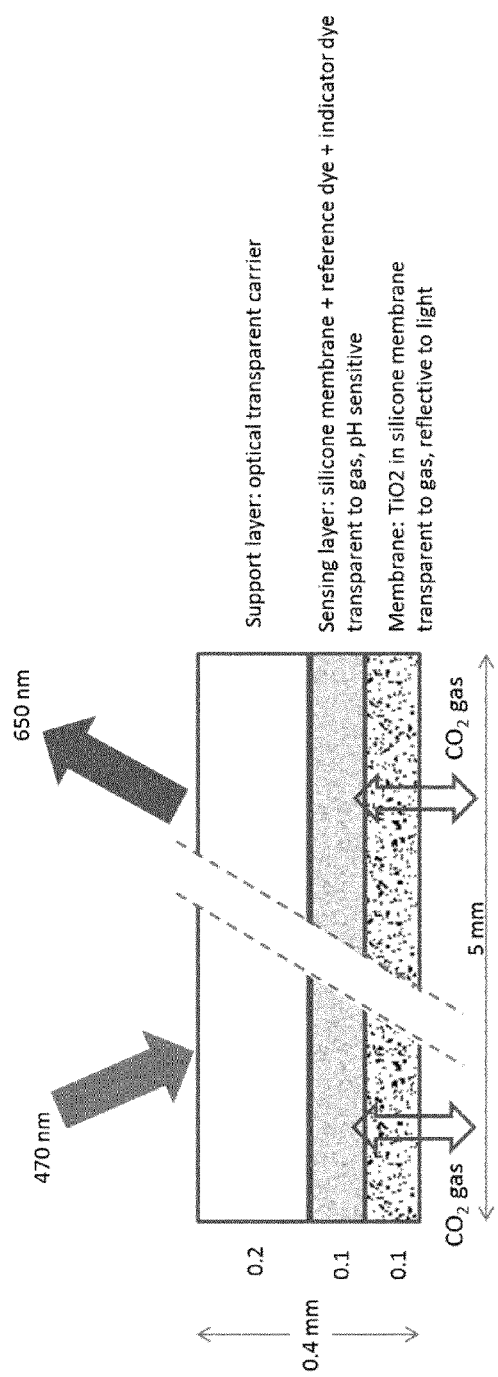
FIG. 1 shows the principles of a chemo-optical sensor for transcutaneous application. The figure depicts a chemo-optical sensor comprising a support layer with an optical transparent carrier, a sensing layer comprising a silicone membrane, a reference dye and an indicator dye, which is transparent to gas and pH sensitive, as well as a layer comprising $TiO_2$ in a silicone membrane, which is transparent to gas and reflective to light. The chemo-optical sensor may, for example, be excited at 470 nm (blue-green LED) and the luminescence may be detected from indicator and reference dyes in the range of 500 to 700 nm (red). The reference dye has a slow response and the luminophores may, for example, be packed in spheres to protect them from $O_2$. The indicator dye has a fast response and it is primary sensitive to $H^+$ (pH), leading to an decrease of the amplitude and a yellow coloring under white light illumination due to pH decrease caused by $CO_2$ increase. The frequency of the illumination light intensity modulation is chosen such that a phase shift at about 45° is obtained at a nominal CO2 concentration.
Figure 2:
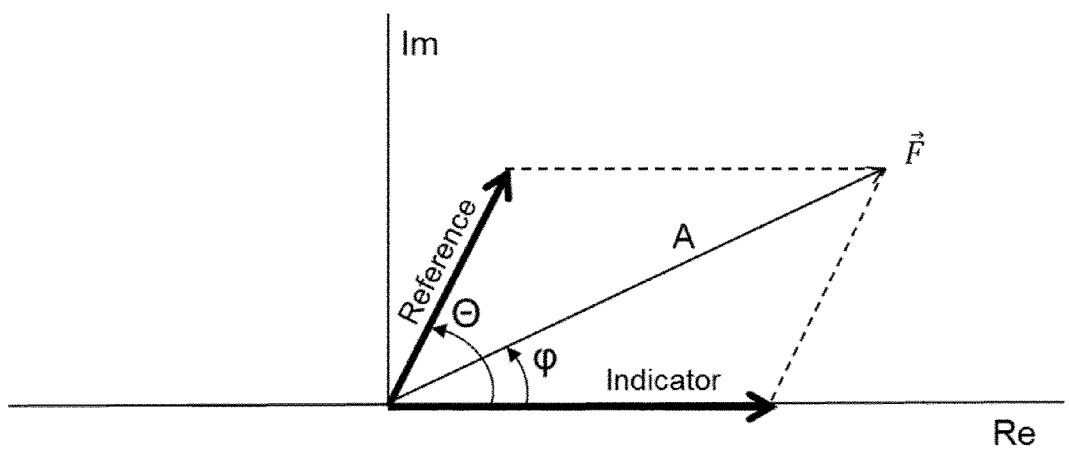
FIG. 2 shows vector diagram of a Dual Life-time Referencing technique (DLR) detection scheme. It is noted that for sake of simplicity in the vector diagram all phase angles are indicated as absolute values, i.e. as positive angles, although in reality the reference dye has a slow response, so that its phase angle is negative and could thus be understood as "–Im".

The present invention relates to methods for detecting inaccuracy of the optically determined concentration of a gas and for correcting such inaccuracy.

Although the present invention will be described with respect to particular embodiments, this description is not to be construed in a limiting sense.

Before describing in detail exemplary embodiments of the present invention, definitions important for understanding the present invention are given.

As used in this specification and in the appended claims, the singular forms of "a" and "an" also include the respective plurals unless the context clearly dictates otherwise.

In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%.

It is to be understood that the term "comprising" is not limiting. For the purposes of the present invention the term "consisting of" is considered to be a preferred embodiment of the term "comprising of". If hereinafter a group is defined to comprise at least a certain number of embodiments, this is meant to also encompass a group which preferably consists of these embodiments only.

Furthermore, the terms "first", "second", "third" or "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

In case the terms "first", "second", "third" or "(a)", "(b)", "(c)", "(d)", "i", "ii" etc. relate to steps of a method or use or assay there is no time or time interval coherence between the steps, i.e. the steps may be carried out simultaneously or there may be time intervals of seconds, minutes, hours, days, weeks, months or even years between such steps, unless otherwise indicated in the application as set forth herein above or below.

It is to be understood that this invention is not limited to the particular methodology, protocols etc. described herein as these may vary. It is also to be understood that the terminology used herein is for the purpose of describing particular embodiments only, and is not intended to limit the scope of the present invention that will be limited only by the appended claims. Unless defined otherwise, all technical and scientific terms used herein have the same meanings as commonly understood by one of ordinary skill in the art.

As has been set out above, the present invention concerns in one aspect a method for optically determining the concentration of a gas, using at least two luminescent dyes, the first being in-sensitive to the concentration of a gas with respect to the luminescence response (reference dye) and the second being sensitive to the concentration of a gas with respect to the luminescence response (indicator dye), wherein said dyes show different luminescence decay times so that the resultant phase angle is indicative for the concentration of a gas, characterized in that the detected luminescent amplitude of the reference dye at a first moment in time is utilized to correct for sensitivity changes after said moment.

The term "concentration of a gas" relates to the amount of gas arriving at a chemo-optical sensor due to diffusion from zones or sectors to be measured. A "gas" may be any gaseous material. It is preferred that the gas is a biologically produced or biologically active or relevant gas, or a biotechnologically produced or biotechnologically relevant gas. Examples of such gases are $O_2$, $CO_2$, $CO$, $N_2$, $NH_3$, $NO$ and $H_2S$. It is preferred that the gas whose concentration should be determined is $O_2$ and/or $CO_2$. It is particularly preferred that the gas whose concentration should be determined is $CO_2$.

The "luminescent dye, being in-sensitive to the concentration of a gas with respect to the luminescence response (reference dye)" may be any luminescent dye which is inert to the increase and/or decrease of the concentration of a gas as mentioned above within the context of a chemo-optical sensor unit to be employed for the measurement. In a preferred embodiment, the reference dye is inert to the increase and/or decrease of the concentration of $O_2$ or $CO_2$ within the context of a sensor unit to be employed for the measurement. Furthermore, the luminescence decay time of the reference dye should be different from the luminescence decay time of an indicator dye as described below. Preferably, a reference dye to be used in the methods of the present invention may have a relatively long luminescence decay time, or a longer luminescence decay time in comparison to an indicator dye as described below. Examples of suitable reference dyes which are inert to a gas and which show a long decay time include: (1) transition metal complexes with ruthenium(II), rhenium (I), or osmium and iridium as central atom and diimine ligands; (2) phosphorescent porphyrins with platinum, palladium, lutetium or tin as central atom; (3) phosphorescent complexes of rare earths, for instance europium, dysprosium or terbium; and (4) phosphorescent crystals such as ruby, Cr-YAG, alexandrite, or phosphorescent mixed oxides such as magnesium fluoro-germanate.

The "luminescent dye, being sensitive to the concentration of a gas with respect to the luminescence response (indicator dye)" may be any luminescent dye which is sensitive to the increase and/or decrease of the concentration of a gas as mentioned above within the context of a chemo-optical sensor unit to be employed for the measurement. In a preferred embodiment, the reference dye is sensitive to the increase and/or decrease of the concentration of $O_2$ or $CO_2$ within the context of a chemo-optical sensor unit to be employed for the measurement. Furthermore, the luminescence decay time of the indicator dye should be different from the luminescence decay time of a reference dye as described above. Preferably, an indicator dye to be used in the methods of the present invention may have a relatively short luminescence decay time, or a shorter luminescence decay time in comparison to a reference dye as described above. For example, an indicator dye may be a fluorescent dye. Examples of suitable indicator dyes which are sensitive to a gas and which show a short decay time include 8-Hydroxypyrene-1,3,6-trisulfonic acid, trisodium salt (HPTS), fluorescein, rhodamine B, rhodamine B-octadecyl ester, hexadecyl-acridine orange, hydroxymethyl coumarin, rhodamine, B-octadecyl ester, rhodamine B, naphthofluorescein, sulforhodamine 101, eosin, thionin, and Nile blue.

In specific embodiments, the present invention relates to combinations of reference dyes and indicators dyes, including all combinations of the above indicated exemplified indicators dyes and references dyes. Preferred examples of combinations of reference dyes and indicators dyes to be used within the context of the methods according to the invention include (reference dye/indicator dye): Ruthenium (II)-(tris-4,7-diphenyl-1,10-phenantroline)/HPTS; Ruthenium(II)-(tris-4,7-diphenyl-1,10-phenantroline)/fluorescein; Ruthenium(II)-(tris-4,7-diphenyl-1,10-phenantroline)/rhodamine B; Ruthenium(II)-(tris-4,7-diphenyl-1,10-phenantroline)/rhodamine B-octadecyl ester; Ruthenium(II)-(tris-4,7-diphenyl-1,10-phenantroline)/hexadecyl-acridine orange; Europium (III)-tris-theonyl-trifluoromethyl acetonate/hydroxymethyl coumarin; Platinum (II)-tetraphenylporphyrin/rhodamine B-octadecyl ester; Platinum (II)-tetraphenyl porphyrin/rhodamine B; Platinum (II)-tetraphenyl porphyrin/naphthofluorescein; Platinum (II)-tetraphenyl porphyrin/sulforhodamine 101; Platinum (II)-octaethyl porphyrin/eosin; Platinum (II)-octaethyl porphyrin/thionin; Platinum (II)-octaethyl ketoporphyrin/Nile blue; CR (III)-YAG/Nile blue; and Cr (III)-YAG/naphthofluorescein.

The methodology of the present invention relies on the measurement of said different luminescent decay times, which translates into a phase shift $\phi$. Specifically, since the reference dye responds slowly on the light modulation, there is as a phase shift $\Theta$ with respect to a real axis which is represented by the light modulation and the fast responding indicator dye are. The phase shift $\Theta$ typically depends on the frequency of the applied light modulation. The phase angle $\phi$ of the resultant vector $\vec{F}$ thus typically only depends on the ratio of the amplitudes of both dyes, and may be linked to the concentration of the gas to be measured on the basis of simple mathematical functions. In other words, the phase angle $\phi$ of the resultant vector $\vec{F}$ is indicative for the concentration of a gas to be measured.

In a preferred example, the phase angle $\phi$ of the resultant vector $\vec{F}$ may be directly linked to the percentage of the gas to be measured, e.g. in the chemo-optical sensor unit. Further examples include the use of a four parameter Boltzmann sigmoid fit in order to fit the total CO2 concentration range from 0 to 100%, e.g. in cases in which such an approach is considered necessary. Further suitable approaches, which are also envisaged by the present invention, include, for example, linear fitting over the concentration range of interest Thus, on the basis of the different decay times of the indicator and the reference dye, the intensity of the excitation may be modulated at a fixed frequency and the phase angle of the luminescence signal, which is independent of the amplitudes, may be detected and translated into a relative intensity of the gas-sensitive indicator dye from which subsequently the gas concentration may be determined. Advantageously, luminescence amplitude effects due to changes in optical transfer function are effectively suppressed because they affect both dyes equally.

In a specific embodiment, the measurement of different luminescent decay times in a reference dye and an indicator dye is essentially based on the Dual Lifetime Referencing principle, e.g. as derivable from U.S. Pat. No. 6,602,716 B1 or from Kocincova, New pH Sensitive Sensor Materials; Luminescent Fiber-Optic Dual Sensors for Non-Invasive and Simultaneous Measurement of pH and pO2 (Dissolved Oxygen) in Biological Systems, 2007, PhD thesis, University of Regensburg.

In a central aspect the present invention provides for an utilization of the detected luminescent amplitude of the reference dye at a first moment for a correction of the detected gas concentration after said moment. This correction thus accounts for sensitivity changes in the measuring process which can be covered by vector de-composition of the luminescent amplitude of the reference dye. The term "correction" as used herein accordingly means that a response from the reference dye as defined herein can be extracted from the measured luminescence by any suitable method of vector-decomposition. Subsequently, a sensor response, i.e. the indication of a gas concentration as describe above, can be compensated on the basis of the luminescent amplitude of the reference dye, which was surprisingly found to correlate well with sensitivity changes due to—but not limited to—osmotic pressure differences between sensor and environment, and introducing e.g. water transport within a chemo-optical sensor unit of the invention. The mathematical de-composition and the subsequent compensation or correction may be carried out according to any suitable mathematical methodology. For example, sinusoidal light excitation and synchronous detection of amplitude and phase may be used. In particularly preferred embodiments, hardware elements may already be implemented to carry out such sinusoidal light excitation and synchronous detection of amplitude and phase. Further envisaged examples include square wave light excitation or the performance of analysis in the time domain, for instance by discriminating the reference dye from its 'longer' impulse response. A further envisaged alternative is analysis in the frequency domain, e.g. by after applying Fourier transformation.

It is preferred that the method of the invention comprises measuring the phase behavior of luminescent responses of said reference and indicator dyes by a single detector, and obtaining a luminescent response vector $\vec{F}$ being independent of the total intensity of both luminescent dyes by the phase behavior measured. This is advantageously followed by a de-composing the measured luminescent response vector $\vec{F}$ into an imaginary part ($\beta$) reflecting solely said reference dye and a real part ($\alpha$) being a summation of the real part of the reference dye and of the indicator dye according to the formula (I)

$$\vec{F} = A\, e^{i\phi} = Re(\vec{F}) + i\, Im(\vec{F}) = A\cos(\omega t) + i\, A\sin(\omega t) = \alpha + i\beta$$

wherein $\alpha$ and $\beta$ are both time variant.

Subsequently, on the basis of the reference dye the measured luminescent response may be compensated. Such a compensation may be carried out according to any suitable algorithm. It is preferred carrying out the compensation according to the formula (II)

$$\alpha' = \frac{\alpha}{1 + k\partial(t)}$$

wherein (III)

$$\partial(t) = \frac{\beta(t) - \beta(0)}{\beta(0)}$$

and wherein k is a function reflecting the sensitivity of the reference dye amplitude versus $CO_2$ sensitivity of said luminescent dyes.

The compensated luminescent response vector is (IV)

$$\vec{F}' = \alpha' + i\beta$$

where its phase angle $\phi'$ is directly linked to the $CO_2$ concentration via the Boltzmann sigmoid.

In a further preferred embodiment, only the indicator dye part of $\alpha$ is compensated (V):

$$\alpha' = \frac{\alpha - \frac{\beta}{\tan\theta}}{1 + k\partial(t)} + \frac{\beta}{\tan\theta}$$

The term "constant reflecting the sensitivity of the reference dye amplitude versus $CO_2$ sensitivity of luminescent dyes" as used herein means that the reference dye and the indicator dye show an experimentally proven sensitivity for certain osmolarities or osmolarity situations. Accordingly derived data may be collected or derived from suitable databases and provided in the form of a suitable constant. The constant may, in further embodiments, be derived directly from current measurements while carrying out the method of the present invention. Accordingly, k may be determined at a first moment in time and subsequently, i.e. during further determination of the concentration of a gas, be used as constant for further calculations during the performance of the method.

In further embodiments, constant k, which reflects a $\beta$-dependence to $CO_2$ sensitivity, may be used as an addition to the 4 Boltzmann calibration constants as mentioned herein above. In a particularly preferred embodiment, the calibration of chemo-optical sensors during manufacturing by applying a range of $CO_2$ concentrations, which may lead to the 4 Boltzmann calibration constants as mentioned herein above, may be extended to a range of different osmolarities. On the basis of such calibration, also a calibration of constant k can be carried out. Subsequently, the concentration of a gas may be determined on the basis of any suitable algorithm or mathematical approach as known to the skilled person. It is preferred, determining the concentration of a gas on the basis of the phase angle $\phi$ of the resultant luminescent response vector $\vec{F}$ (IV)

$$\vec{F} = \alpha' + i\beta.$$

The determination may be carried out according to any suitable mathematical methodology. For example, sinusoidal light excitation and synchronous detection of amplitude and phase may be used. Further envisaged examples include square wave light excitation or the performance of analysis in the time domain, for instance by discriminating the reference dye from its 'longer' impulse response. A further envisaged alternative is analysis in the frequency domain, e.g. by after applying Fourier transformation.

In a further, specific embodiment of the present invention the imaginary part ($\beta$) and the real part ($\alpha$) of the measured luminescence response of the measured luminescence response are filtered. Such a filtering may, for example, be a low-pass filtering, which can be implemented electronically, e.g. with suitable filtering algorithms or on the basis of suitable devices. Accordingly, the filter or filtering passes low-frequency signals and reduces the amplitude of signals with frequencies higher than a cutoff frequency. In preferred embodiments, the ($\beta$) part, which may be used for correction, may be low pass filtered. In certain embodiments the filtering may be carried out in a range reflecting the slowness of osmotic effects, which may take place in time frames of in about 10 min to several hours. In alternative embodiments, the ($\beta$) part may be used for detecting measurement artifacts, e.g. water loss etc., which occur more rapidly. In these cases, the ($\beta$) part may be used without filtering or almost unfiltered to suitably detect such fast occurring fluctuations.

As outlined above, the present invention allows the determination of a steady state ratio between the luminescence of the reference dye and of the indicator dye according to the vector decomposition approaches described. Advantageously, such steady state ratio may be determined in a certain environment, e.g. the skin of human subject, a biotechnological device etc. On the basis of the determined state sate ratio of the luminescence of the reference dye and of the indicator dye a calibration status may be defined for a chemo-optical sensor as described herein. Such calibration status may subsequently be used for the calibration of (i) other chemo-optical sensors of the same make-up in (ii) the same environment, or in (iii) different environments, e.g. different osmotic environments. Accordingly, steady state information which constitutes the essence of correction calculations for gas concentration measurements in a specific situation may be employed as starting points for suitable calibration approaches in new environments. The corresponding calculation may further be adapted or modified according to additional constants reflecting each specific environment. For example, the determination of a steady state ratio between the luminescence of the reference dye and of the indicator dye according to the vector decomposition approaches described herein may lead to constant k as described herein above which may be used for calibration purposes. Further alternative approaches to provide such constant k are also possible and envisaged by the present invention. In a preferred embodiment the constant k may be a non-linear function of the reference dye intensity. In a particularly preferred embodiment he constant k is a non-linear function of the reference dye intensity and can be calibrated in a range of osmolarities. These approaches may vary according to the correction method used, as outlined herein.

Constant k may, for example, be used as further parameter in the calibration process, which may advantageously reflect the response of the dyes to osmolarity changes with respect to the osmolarity in its environment, e.g. in the packaging.

In further, alternative embodiments, one or more calibration Boltzmann constants may be adapted by the reference dye amplitude.

The present invention further envisages a method wherein the dynamics of the steady state ratio between the luminescence of the reference dye and of the indicator dye in one osmotic environment are used as calibrator for the dynamics of changing osmotic environments. The term "dynamics of the steady state ratio" as used herein refers to a mathematical refection or description of the steady state ratio observed, in particular of the steady state ratio of the luminescence of the reference dye and of the indicator dye as described herein above. By providing a mathematical description of the observed behavior, the derived model may advantageously be used for calibration purposes for similar or identical situation. Preferably, the model may be used as calibrator for different environments. More preferably, the model may be used as prediction model for changing osmotic situations.

In an illustrative embodiment the sensors may be used in the following non limiting and only illustrative scenario: first, the sensor unit may be calibrated during the manufacturing process for a range of different osmolarities and $CO_2$ concentrations. Furthermore, the resulting vector may be measured, e.g. after packaging of the sensor unit. Typically, this may be done together with a contact fluid necessary to use the sensor unit on a skin surface. The sensor unit may thus be well characterized. During shelf life of the sensor, i.e. during the time period in which the sensor unit is not used, the proper and accurate characterization of the sensor may dwindle. This may be due to factors such as the loss of water from the sensor unit (or from contact fluid) into packaging material. Accordingly, after having unpacked the sensor unit and briefly before using the sensor unit or after having applied the sensor unit to the skin, i.e. in the time frame of the initial using of the sensor unit when slow effects due to $CO_2$ entry or osmosis from the skin have not yet become perceptible, a resulting luminescent vector may be measured.

This luminescent vector may advantageously be used for an initial measurement quality assessment. This quality measurement may, for example, be used to detect if the sensor is placed or stored properly and/or connected properly, e.g. to the read-out unit. The measured vector may accordingly be used for comparisons with the manufacturer's calibration data after packaging. Thus, on basis of deviations from the manufacturer's calibration (after packaging) the presence of storage or connection problems may be detected. Accordingly, the question whether the light transmission is correct or not may be answered.

In a further additional or alternative embodiment, the luminescent vector may be employed as t=0 reference measurement. Such reference measurement may be used for sensor measurements activities to be performed. Preferably, the measurement would be an upcoming transcutaneous measurement.

In specific embodiments of the present invention the reference and the indicator dye as defined herein above may absorb light in the same range of wavelengths. This allows to excite them into luminescence by means of only one single light source. Accordingly, in a specific embodiment of the present invention the luminescent dyes are excited by a single light source. This light source is preferably adapted to irradiate the reference and the indicator dyes according to their chemical and optical properties. The light source may accordingly provide radiation in a predetermined wavelength, preferably light in an excitation wavelength or range of wavelengths adapted to the reference and the indicator dyes as mentioned herein above. The light source may have any suitable form, provide any suitable intensity and provide any suitable wavelength(s). In a specific embodiment the light source may preferably be a light emitting diode (LED).

In a further embodiment, the excitation of the reference and the indicator dye is a simultaneous excitation. Thus, on the basis of only one light source and being excitable by the same wavelengths or range of wavelengths, the reference and indicator dye can be excited at the same time.

The luminescent dyes may be provided in any suitable form or context. It is preferred having the dyes organized in chemo-optical sensor unit. Such a sensor-unit may, for example, comprise a sensing layer which comprises the reference and the indicator dye. The term "sensing layer" as used herein thus refers to a layer which may be irradiated or excited and which may subsequently generate a light of a different wavelength due to the excitation of an optically reactive material, e.g. luminescence such as fluorescence, as optical response. The sensing layer may be composed of filler material which is passable for gas molecules. An example of such filler material is silicone rubber material. In a specific embodiment, the sensing layer may comprise silicone rubber or essentially consist of silicon rubber material. The sensing layer may further comprise compounds such as water or chemical buffers. The sensing layer may accordingly be buffered at a specific pH or comprise a certain amount of protons and/or hydroxide ions, e.g. have a certain pH. The pH which may be changed due to the diffusion of gases, in particular $CO_2$ into the sensing layer. Preferably, $CO_2$ may diffuse into the sensing layer and change the pH in said sending layer by interacting with water, thus increasing the concentration of protons and thus changing the pH.

The term "irradiated with a predetermined radiation" as used herein means that the sensing layer may be irradiated or excited with radiation of a suitable wavelength, in particular a wavelength which is able to generate an optical response of the sensing layer. For example, the irradiation may be carried out with visible light, infrared light and/or ultraviolet light. Preferred examples of a predetermined radiation is light of the green-blue visible spectrum, e.g. of a wavelength of about 400 to 500 nm, e.g. 440 nm, 450 nm, 460 nm, 470 nm, 480 nm, 490 nm etc. The radiation, i.e. the light wavelength as well its intensity, may in general be made dependent on or be adapted to the indicator and the reference dye in the sensing layer. For specific optically reactive material suitable corresponding excitation wavelengths may be used. It is further preferred that the emission spectra of the indicator and the reference dye are in the same spectral region. Thus, for example, if the reference and the indicator dyes are excited with light of a wavelength of about 450 nm, one dye might emit green light, e.g. at 520 nm and the other may emit red light, e.g. at 600 nm. Such a narrow range of emission spectra may be detectable with one optical detector, thus allowing for a cost sensitive implementation.

Within the context of the chemo-optical sensor unit the sensing layer is adapted to measure an optical response of the at least one sensing layer, whose optical response depends on the concentration of the gas.

In a preferred embodiment, the sensing layer comprises as optically reactive material a reference dye and an indicator dye as described herein above. In particular, a combination of reference dyes and indicator dyes as described herein above may be present in the sensing layer.

The sensing layer may further be at least passable for gas molecules such as $O_2$ and/or $CO_2$, which may arrive from a deeper layer such as the gas-permeable layer. Typically, the sensing layer may also be permeable for water molecules, which may diffuse in or out of deeper layers, i.e. layers below the sensing layer according to the osmotic pressure in the corresponding region of the chemo-optical sensor according to the present invention.

In certain specific embodiments, the sensing layer may comprise luminescent material which is capable of measuring the concentration of different gases, or which is capable of measuring the concentration of more than one gas simultaneously, e.g. the concentration of two gases at the same time. For example, the sensing layer may comprise two kinds of luminescent material adapted to the measurement of a different gas, respectively. Preferably, one sub-layer, region or one kind of material may be adapted to detect oxygen and a second sub-layer, region or kind of material is adapted to detect $CO_2$. Further details on multiparameter sensors and additional possibilities of implementing them would be known to the skilled person or can be derive from suitable literature sources such as WO 02/056023 or Schäferling, The Art of Fluorescence Imaging with Chemical Sensors, 2012, Angewandte Chemie International Edition, 51(15), 3532-3554.

The sensing layer may be provided as single layer. In alternative embodiments more than one sensing layer may be provided. Such second or further sensing layer may have the same properties or different properties than the first sensing layer. For example, the second or further sensing layer may comprise different luminescent material, e.g. different dyes, or it may be provided in a different chemical environment such as a different buffer, or having a different pH than a first sensing layer. In further embodiments, a second or subsequent sensing layer may be adapted to measure a different gas, than a first sensing layer, e.g. $O_2$ instead of $CO_2$ which may be measured in a first sensing layer.

The chemo-optical sensor unit may further be adapted to measure an optical response of the at least one sensing layer. Importantly, the received optical response is supposed to depend on the concentration of the gas to be measured. Such an adaption may comprise the provision of suitable detection methods or devices allowing to receive, detect and/or analyze one or more optical responses emanating from the sensing layer. The detection may be performed or implemented according to any suitable detection methods or on the basis of any suitable detection devices or comprising suitable components allowing to perform detection steps or sub-steps.

In a further embodiment, the chemo-optical sensor comprises, adjacent to the sensing layer, at least one gas-permeable layer. The term "gas-permeable layer" as used herein refers to a structure which is passable for gas molecules. Typically, the gas-permeable layer is provided as a membrane structure which is adapted to pass gas to the overlaying sensing layer. In specific embodiments, the gas-permeable layer is passable for gas molecules such as $O_2$ and/or $CO_2$. Typically, the gas-permeable layer may also be permeable for water molecules, which may diffuse in or out of layers above or below the gas-permeable layer, e.g. according to the osmotic pressure in the region of the chemo-optical sensor according to the present invention. Such diffusion process or transport of water molecules may, for example, be accomplished on the basis of water in the gas-phase.

The membrane of the gas-permeable layer may be composed of suitable gas and water permeable material. For example, the membrane may be a silicone membrane, or may comprise silicone. Alternatively, the membrane may be composed of or comprise materials such as PTFE (telfon) or derivatives. In further alternative embodiments, the membrane may be composed of or comprise a metal mesh, porous hydrophobic polymers, e.g. based on polypropylene and ethylene, porous hydrophobic siliconoxides such as areogels, or perfluoro materials such as nafion. Further suitable material would be known to the skilled person and are also envisaged in the context of the present invention.

The gas-permeable layer may further be composed of filler material which is passable for gas molecules. An example of such filler material is silicone rubber material. In a preferred embodiment, the gas-permeable layer may thus comprise silicone rubber or essentially consist of silicon rubber material.

In further preferred embodiments of the present invention, the gas-permeable layer may additionally be adapted to prevent light from passing through the gas-permeable layer. The term "preventing light from passing through the gas-permeable layer" is in particular intended to mean that the gas permeable layer is be adapted to reflect or scatter light transmitted through the at least one sensing layer, and/or to block possible light interferences outside of the intended sensor range. The reflection or scattering of light by the gas permeable layer may be achieved by using any suitable light reflecting material such as metals, e.g. aluminium, or metal oxides. Particularly preferred is the use of titanium compositions, e.g. compositions comprising $TiO_2$. In specific embodiments, the light reflection or scattering may be complete, i.e. for all wavelengths, or it may be specific for certain wavelengths or ranges of wavelengths. For example, light of a certain wavelength or range of wavelengths, in particular of the excitation wavelength for the luminescent material in the sensing layer, may be reflected or scattered, whereas light of a different wavelength which is not excitatory for the luminescent material in the sensing layer may not be reflected. In further embodiments, the light reflection or scattering may be dependent on specific parameters, e.g. temperature, pH, presence of gas molecules, presence of polar compounds etc. at the gas-permeable layer. Further, the gas permeable layer may block possible interference of fluorescent molecules, for example outside of the intended sensor range. In a preferred embodiment, the blocking of interference of fluorescent molecules may be a blocking of fluorescence outside of a range of about 400 nm-700 nm. Such a blocking activity may be accomplished by providing light absorbing materials, which work outside of the envisaged sensing range.

The gas-permeable layer may thus essentially function as barrier to light, as permeable layer for small molecules such as $CO_2$, $O_2$ or $H_2O$, and as semi-active, i.e. strongly retarding, barrier to larger molecules, in particular a first compound other than water according to the present invention, which may have a low polarity. In another specific embodiment, the gas-permeable layer is provided in the form of a barrier layer without any water and still a high gas permeation property. Such a gas-permeable layer may comprise silicone oil, soft silicone rubber, perfluoroalkane oil, soft perfluoro (teflon) rubbers or edible oils, or derivatives thereof, or any combination of these compounds.

The gas-permeable layer may be provided as single layer. In alternative embodiments more than one gas-permeable layer may be provided. Such second or further gas-permeable layer may have the same properties as, or different properties than the first gas-permeable layer. For example, the second or further gas-permeable layer may have the property of reflecting light of a different wavelength. In further embodiments, the second or further gas-permeable layer may have the property of being permeable for different molecules than the first gas-permeable layer. E.g. different gases, or different compounds may pass through the first and second or subsequent gas-permeable layer.

In further specific embodiments of the invention the chemo-optical sensor may further comprise at least one optical transparent layer adjacent to the at least one sensing layer. The optical transparent layer may preferably be on top of the sensing layer, which in turn is on top of the gas-permeable layer as defined herein above. The transparent layer may accordingly cover the sensing layer and protect it from direct contact with the surrounding atmosphere. Thus, the at least one sensing layer may be enclosed by the gas permeable layer from one side and by the optical transparent layer from the other side. The term "optical transparent layer" as used herein refers to a carrier substrate which is at least partially transparent for radiation. In some embodiments, the optically transparent layer may be transparent for the entire suitable spectrum of electromagnetic waves, e g infrared light, visible light and ultraviolet light. In other embodiments, the optically transparent layer may be transparent for specific wavelengths or wavelength ranges only. The optical transparent layer may for example be transparent for the predetermined radiation as described above, or excitation wavelength(s) or wavelengths range(s) for the luminescent material(s) in the sensing layer, whereas light of a different wavelength which is not excitatory for the luminescent material in the sensing layer may not be passed. In addition, the optical transparent layer may be transparent for the light of the optical response generated in the sensing layer. Such light may be provided in a specific wavelength or range of wavelength which may specifically be passed through the optical transparent layer, whereas light of different wavelengths may be passed. In a specific embodiment, the optical transparent layer may only be transparent for excitation wavelength(s) or ranges of wavelength(s) for the luminescent material in the sensing layer and for the wavelength(s) or range of wavelength(s) generated as optical response by said luminescent material in the sensing layer.

The optical transparent layer may, for example, be composed of transparent material such as glas, polycarbonate, PET, silicone rubber, or PMMA (plexiglas).

In further embodiments, the optical transparent layer may be non-permeable for gas, e.g. for $O_2$ and/or $CO_2$. In further embodiments, the optical transparent layer may further low-permeable for water and/or a first compound other than water according to the present invention.

In a further embodiment, the optical sensor is adapted to operate with a contact medium. The term "contact medium" as used herein refers to a medium which may be provided at the interface between the chemo-optical sensor unit and the surface layer on which the measurement of gas is to be carried out, e.g. the skin. Preferably, the contact medium is interposed at least between the gas-permeable layer as defined herein above and the surface layer on which the measurement of gas is to be carried out, i.e. the skin of the human or animal body. The contact medium may be a gel or liquid, which typically allows to transfer gas molecules from the deeper layer, e.g. skin, to the chemo-optical sensor unit according to the present invention. Thus, in a particularly preferred embodiment, the contact medium is at least gas-permeable. The gas-permeability may be a general permeability for any gaseous material. Alternatively, the contact medium may have a specific permeability for certain gas molecules, e.g. for $O_2$, $CO_2$, $CO$, $N_2$, or $NH_3$, $NO$, or $H_2S$. Particularly preferred is the permeability for $O_2$ and/or $CO_2$. Most preferred is the permeability for $CO_2$. In specific embodiments, the contact medium may be selectively permeable for certain gases and impermeable for other gases. It is preferred that the contact medium by selectively permeable for at least $O_2$ and/or $CO_2$. Most preferred is a selective permeability for $CO_2$. Furthermore, the contact medium may allow to keep the water content or moisture content of the surface layer on which the measurement of gas is to be carried out stable, or to control the water content or moisture content of the surface layer on which the measurement of gas is to be carried out, e.g. the skin of the human or animal body.

The contact medium may further be characterized as being biocompatible. The term "biocompatible" as used herein means that the contact medium does not cause a toxic, immunologic, and/or allergic reaction to the surface area of the skin of the human or animal body to which it is applied, or to the body of the person to which it is applied, or any other biologically or medicinal deleterious or harmful reaction, e.g. that it is not carcinogenic.

In addition, the contact medium may be thermally conductive. The thermal conductivity may be used to mitigate thermal changes of the chemo-optical sensor unit, i.e. to minimize a temperature difference between the chemo-optical sensor and the skin area underlying the contact medium. Thereby a constant temperature at the chemo-optical sensor unit can be achieved, thus allowing for an improved measurement of the concentration of a gas.

Figure 6A:
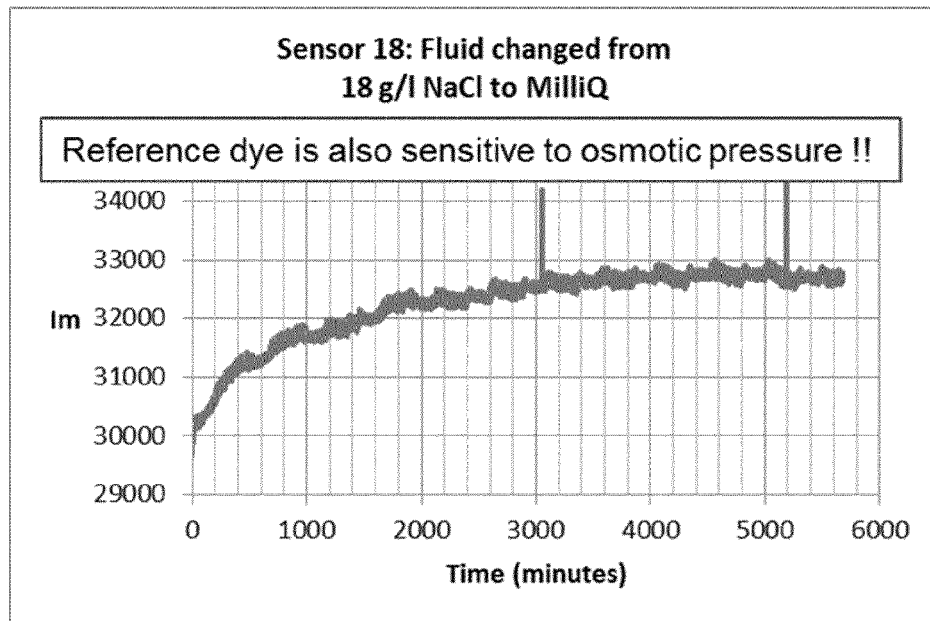
FIG. 6 shows Imaginary (FIG. 6A) and Real parts (FIG. 6B) of the luminescence after transfer of the sensor spot into a lower (zero) osmotic environment.
Figure 9A:
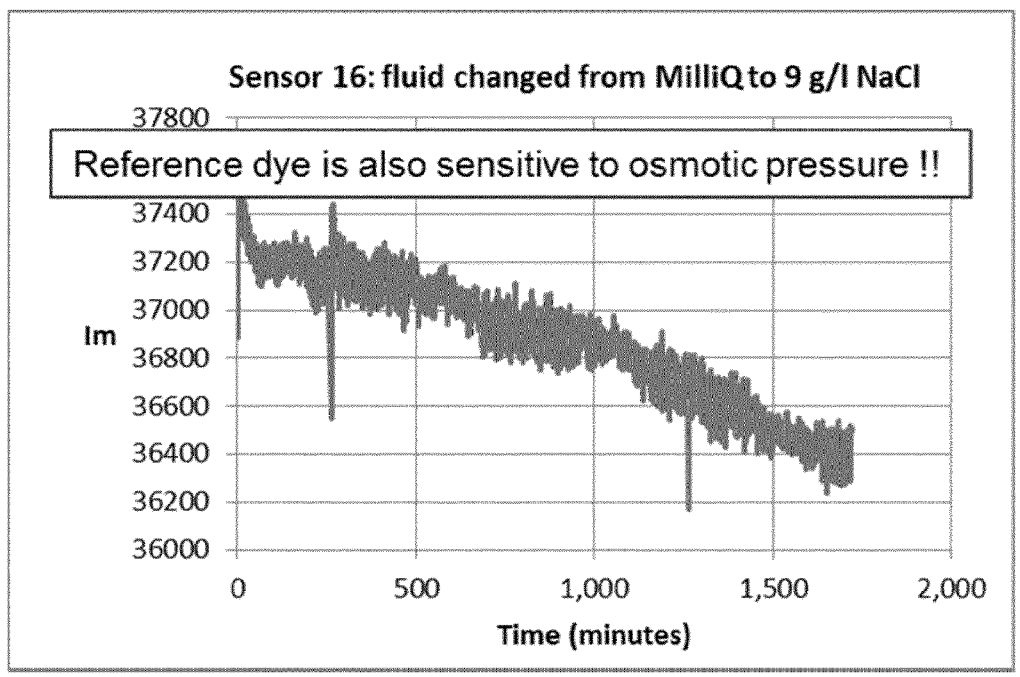
FIG. 9 shows Imaginary (FIG. 9A) and Real parts (FIG. 9B) of the luminescence after transfer of the sensor spot into a higher osmotic environment.

In a further central aspect the invention relates to a method for quality assessment of the measurement of an optical sensor for determining the concentration of a gas. The method is basically based on measurement steps as outlined above, which allow to determine whether the luminescent amplitude of the reference dye changes after an initial moment. Corresponding extraction experiments are described in Examples 3 and 5 and FIGS. 6A and 9A, infra. If so, i.e. if there is a sensitivity change detected when carrying out the measurement of gas concentrations as outlined above, the measured values may be disregarded from further use. In further embodiments, a detected sensitivity change may lead to a removal of the sensor used, or may induce a re-calibration or calibration activity. Alternatively, quality ensuring counter-actions may be started. One option would be the correction of the detected sensitivity change according to the correction approach as defined herein above. The quality assessment method of the present invention thus largely concentrates on the detection of sensitivity changes, which give rise to quality problems of the underlying measurement or of the use of the sensor in said measurement. The quality assessment approach may be based on the methodology as described herein. Preferably, it comprises the use of at least two luminescent dyes, the first being in-sensitive to the concentration of a gas with respect to the luminescence response (reference dye) and the second being sensitive to the concentration of a gas with respect to the luminescence response (indicator dye), wherein said dyes show different luminescence decay times so that the resultant phase angle is indicative for the concentration of a gas. The detected luminescent amplitude of the reference dye at a first moment in time may accordingly be utilized for the indication or detection of sensitivity changes after said moment.

In a further embodiment of the present invention the sensitivity change may also be due to a vertical thermal gradient. The gradient may preferably be in a direction perpendicular to the sensor surface. Such gradient may be caused by different factors depending on the use of the sensor unit. For example, the vertical thermal gradient may be caused by a skin heating system. Such skin heating systems would be known to the skilled person. A chemo-optical sensor unit as described herein may, in one example, be part of the skin heating system. The skin heating system may typically be used to achieve arteralisation during a transcutaneous gas measurement on the skin. By having or developing a vertical thermal gradient a water transport in the zone where said gradient is present may occur. Due to the water transport the sensor sensitivity may change. This detection of a sensitivity change due to a vertical thermal gradient may either lead to a removal of the sensor used, or may induce a re-calibration or calibration activity. Alternatively, a quality ensuring counter-action may be started, in particular, the detected sensitivity change may be corrected or compensated according to the correction approach as defined herein above. In a particularly preferred embodiment, the quality assessment comprises the determination of an imaginary part ($\beta$) according to formula (I)

$$\vec{F} = A\, e^{i\phi} = Re(\vec{F}) + i\, Im(\vec{F}) = A\cos(\omega t) + i\, A\sin(\omega t) = \alpha + i\beta$$

wherein $\alpha$ and $\beta$ are both time variant, wherein a real part ($\alpha$) is a summation of the real part of the reference dye and of the indicator dye. Having obtained these values, the imaginary part of the luminescence response ($\beta$) may further be analysed, e.g. over time or over several measurements. For example, if there is a slow and/or gradual variation of said imaginary part ($\beta$) detectable, this would be indicative of an acceptable measurement quality. On the other hand, if there is a fast changing or fluctuating variation of said imaginary part ($\beta$) detectable, this would be indicative of a non-acceptable measurement quality.

The term "slow and/or gradual variation of the imaginary part" as used herein refers to situations in which osmotic changes occur in a fluid, for examples during transcutaneous application of a chemo-optical sensor. These changes have an influence of the Im part as defined herein above on a larger time scale such as several minutes to several hours or days, e.g. 30 min, 40 min, 50 min, 60 min, 1 h, 2 h, 3 h, 4 h, 5 h, 6 h, 1 day, 2 days, 3 days or any value in between the mentioned values.

The term "fast changing or fluctuating variation of the imaginary part" as used herein refers to situations in which rapid changes occur, e.g. the sensor dries out, for example due to improper fluidic contact or the like. In such cases the change of the Im part is a fast change or fluctuation in the range of minutes up to an hour, e.g. 1 min, 2 mins, 3 mins, 5 mins, 10 mins, 20 mins, 30 mines etc. or any value in between the mentioned values.

Sensitivity changes which can be detected and/or be corrected according to the present invention may be associated with any location or position, where a chemo-optical sensor as described herein may suitably be used. In further embodiments, sensitivity changes which can be detected and/or corrected on the basis of the herein provided methodology may also be associated with further detector devices which are essentially based on the use of luminescence responses from reference and indicator dyes with different sensitivity to gas concentration. Examples include the measurement of gas concentration with chemo-optical sensors in medical environments, e.g. the gas measurement of a patient or subject, or in biotechnological environments, e.g. for the monitoring of gas production in fermenters or the like. Typically, sensitivity changes may be detected and/or corrected which occur in osmotically unbalanced environments. Examples of such environments include a body surface. It is particularly preferred that such sensitivity changes occur when measuring gas concentrations at the human or animal skin, i.e. in transcutaneous gas measurement approaches carried out on the human or animal skin.

In preferred embodiments, the gas concentration to be measured is a blood gas concentration. The term "blood gas" as used herein refers to gaseous materials present in the blood and capable of exiting a body, which can be measured, e.g. over the skin. The measurement is such that a chemically exact reflection of the gas content of blood is obtainable. The preferred blood gas concentrations to be measured are the concentrations of $O_2$ or $CO_2$. Particularly preferred is the measurement of the concentration of $CO_2$.

The most preferred application of the methodology according to the present invention is the correction of determined gas concentrations of $CO_2$ in a transcutaneous measurement at the skin of a human being. The present invention further envisages the detection of sensitivity changes and the corresponding assessment of the quality of the measurement as defined herein above in the determination of CO2 gas concentrations in a transcutaneous measurement at the skin of a human being.

The chemo-optical sensor unit as mentioned herein above, which is preferably used for the described measurements of gas concentrations, is accordingly provided as a transcutaneous sensor unit. It can thus be applied to the skin of an animal or human being. Accordingly, the sensor is capable of measuring blood gas concentrations of a subject via the subject's skin, wherein blood gas may diffuse via the skin into the chemo-optical sensor unit, optionally passing a contact medium as defined herein above.

The chemo-optical sensor unit as mentioned herein above, which is preferably used for the described measurements of gas concentrations may further comprise additional components or be combined with additional components in order to facilitate or improve the measurement. For example, the chemo-optical sensor may be combined with or comprise at least one light source which is adapted to irradiate the sensing layer as defined herein above. The light source is preferably a single light source, e.g. in the form of a light emitting diode (LED). Such a light source may further be combined with a light guiding structure. The light guiding structure may be arranged, for example, above the sensing layer/optically transparent layer of the chemo-optical sensor and may be connected to a light source external to the chemo-optical sensor unit. Light from an external light source may be introduced into the light guiding structure, which is adapted to direct said light towards the at least one sensing layer. The light-guiding structure may comprise any suitable light guiding material. Preferably, optical fibers may be used as light guiding material, which may be provided in the form of light-guiding structures. Optical fibers may accordingly be provided as single fibers, or as fiber bundles. A light source, being connected to a light guiding structure, may thus be used to irradiate the sensing layer of a chemo-optical sensor unit according to the present invention, although being located externally. In further embodiments, a light source may be connected to more than one chemo-optical sensor unit via light guiding structures arriving at distinct chemo-optical sensor units. The chemo-optical sensor may further be combined with a detection device. Such a detection device, for instance a photosensitive device, may be capable of sensing an optical response coming from the sensing layer and may be adapted to generate signals, e.g. electrical signals, corresponding to the sensed optical response. The signals may further be transmitted to an external apparatus for subsequent analysis. The detection device may be adapted to the optical response expected from the sensing layer, e.g. provided by a dye or a combination of dyes as described herein above. The detection device may further be combined via a light guiding structure to the chemo-optical sensor unit as defined herein. In specific embodiments the same light guiding structure, which provides light from the light source to the sensing layer, may be used to collect the optical response of the sensing layer and to guide said optical response, for instance fluorescent light, via the same or a different optical fiber to a detection device or an apparatus external to the chemo-optical sensor unit for analysis. By using light guiding structures it is thus possible to connect an input and/or output light guiding structure, which is/are coupled to the chemo-optical sensor unit. In this embodiment no additional unit needs to be connected to the chemo-optical sensor unit accommodating the light source and the at least one detection device.

Further, the at least one light source and the at least one detection device may form a unit. This unit may in a further preferred embodiment be detachably connected to the chemo-optical sensor unit, e.g. by a housing or structure. Accordingly, certain parts of the chemo-optical sensor unit, for instance the sensing layer, gas permeable layer, or a housing and/or supporting structure of the chemo-optical sensor unit may be disposable, whereas other parts of the optical sensor such as the light source and the detection device, or the light guiding structures and may be reused. In specific embodiments, the chemo-optical sensor unit may be composed of two devices or two parts, a disposable or cartridge part and a non-disposable or reusable part. In particular, the disposable or cartridge part may work as passive device and not include any expensive electronics at all. Hence, this part may be manufactured with low effort thereby reducing costs, whereas the second, non-disposable part may include the electronics or optical elements and be reused. It may accordingly also be used with different disposable parts, e.g. allowing to measure the concentration of different gases (for instance $O_2$ and $CO_2$). Thereby an increased flexibility of the chemo-optical sensor unit can be provided.

Another example of an additional component, which may be combined with the chemo-optical sensor as described above is a heating element.

Further, the chemo-optical sensor may be provided in the form of a system for patient monitoring and/or ventilation of a patient, comprising a chemo-optical sensor unit as defined herein above, a ventilation device and/or a monitoring device. The monitoring device may, for example, include optoelectronics for supplying the chemo-optical sensor unit with light via optical fibers, and for receiving luminescent light from the sensing layer. The monitoring device may further comprise means for determining/calculating a gas concentration based on the received optical response, and for potentially correcting the obtained measurement results according to the above described methodology. Such a monitoring device may comprise further elements such as a heater controller for controlling the temperature of the heating element, or means for communication with the ventilation device. Further possibilities of connecting the monitoring device or of combining the device with additional components would be known to the skilled person and are envisaged by the present invention.

The following examples and figures are provided for illustrative purposes. It is thus understood that the examples and figures are not to be construed as limiting. The skilled person in the art will clearly be able to envisage further modifications of the principles laid out herein.

EXAMPLES

Example 1

Osmotic Pressure Variations; Transfer to Zero-osmolality Demi-water

Figure 3:
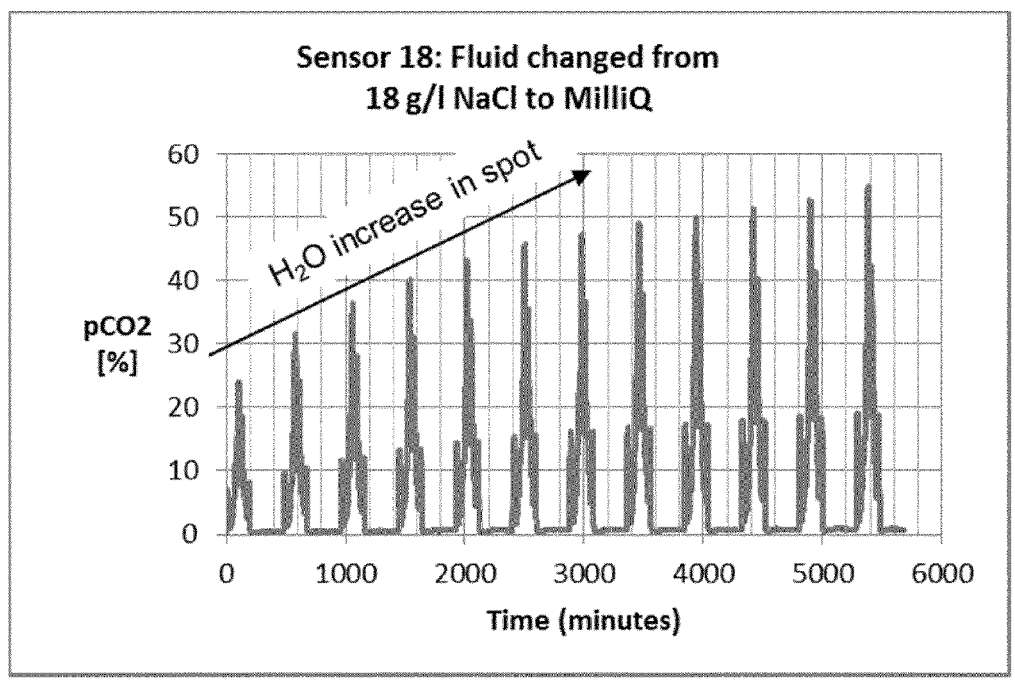
FIG. 3 shows $pCO_2$ after transfer of the sensor spot into a lower (zero) osmotic environment.

In a first experiment a sensor spot was conditioned in 18 g/l NaCl, which is twice the nominal physiological osmotic pressure for which the sensor is typically designed for. At t=0 the sensor is transferred into zero-osmolality demi-water and bubbled with varying concentrations of $CO_2$. According to physics, water travels into the spot in an attempt to balance the osmotic pressure in- and outside the spot. As a result the sensitivity increases, most probably by the fact that more $H_3O^+$ ions become available to react with the pH sensitive indicator dye (see also FIG. 3).

Example 2

Osmotic Pressure Variations; Transfer to Physiological Saline Solution

Figure 4:
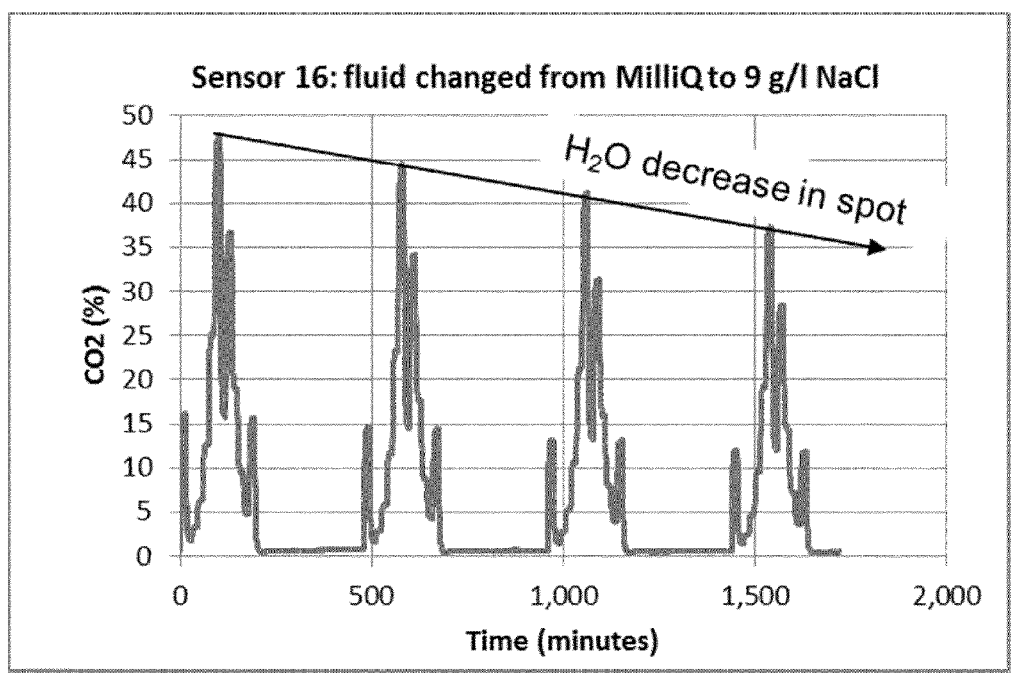
FIG. 4 shows $pCO_2$ after transfer of the sensor spot from demi-water into physiological saline.

In a second experiment the spot was transferred from a demi water conditioning fluid into a physiological saline solution. Now water moves out from the sensor spot and the sensitivity drops (see also FIG. 4).

Example 3

Extraction of Response from Reference Dye

Figure 5:
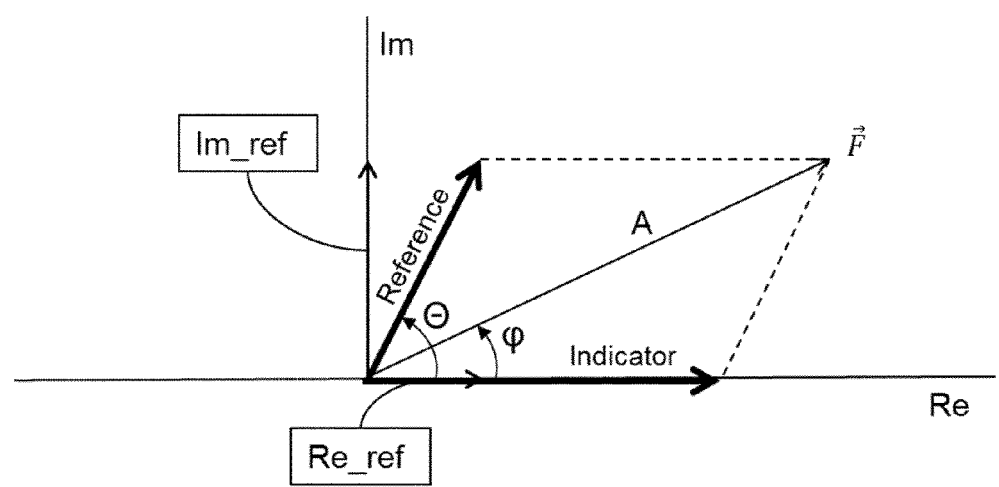
FIG. 5 shows the Imaginary $Im(\vec{F})$ and the Real $Re(\vec{F})$ parts of the luminescence vector $\vec{F}$ as a function over time for the experiments described in Examples 1 and 2. It is noted that for sake of simplicity in the vector diagram all phase angles are indicated as absolute values, i.e. as positive angles, although in reality the reference dye has a slow response, so that its phase angle is negative and could thus be understood as "–Im".

The response from the reference dye in Example 1 was extracted from the fluorescence by vector de-composition (see also FIG. 5) according to $$\vec{F} = A\, e^{i\phi} = Re(\vec{F}) + i\, Im(\vec{F}) = A\cos(\omega t) + i\, A\sin(\omega t) = \alpha + i\beta$$

Figure 6B:
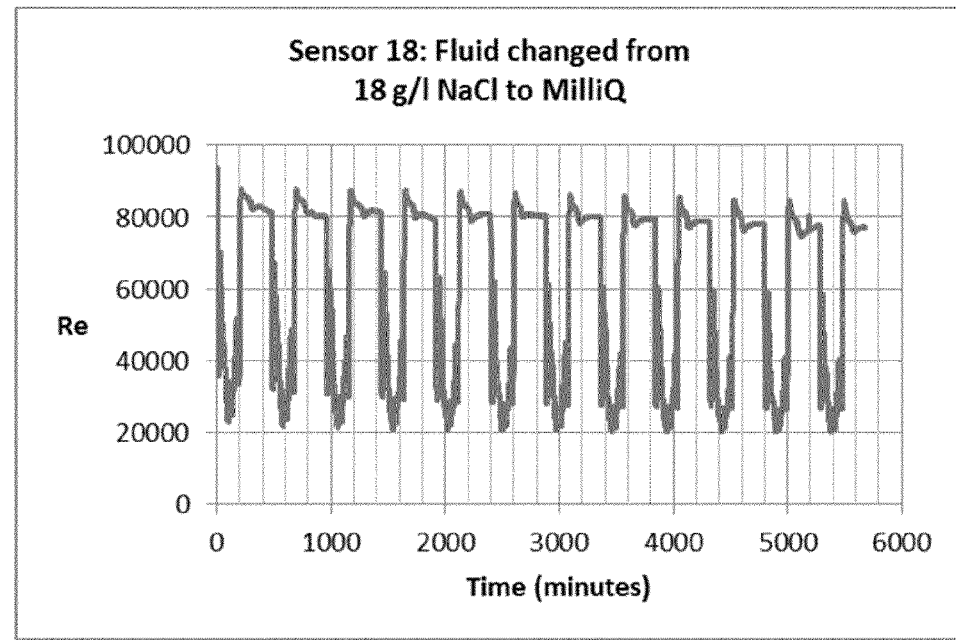

The Imaginary part was insensitive for the applied $CO_2$ modulation and shows an exponential-like increase to a constant level after ~4000 minutes (see also FIG. 6 A), which is explainable as water transport until the osmotic pressure in- and outside the sensor has been balanced.

Example 4

Compensation of Sensor Response

In a next step the sensor response of Example 1 was compensated on basis of the reference dye. First, the relative change $\partial(t)$ of the imaginary part (representing the reference dye) was calculated according to:

$$\partial(t) = \frac{\beta(t) - \beta(0)}{\beta(0)}$$

This value was used to correct the Real part according to:

$$k\partial(t) = \frac{\alpha(t) - \alpha'(t)}{\alpha'(t)} \Longrightarrow \alpha'(t) = \frac{\alpha(t)}{1 + k\partial(t)}$$

Figure 7A:
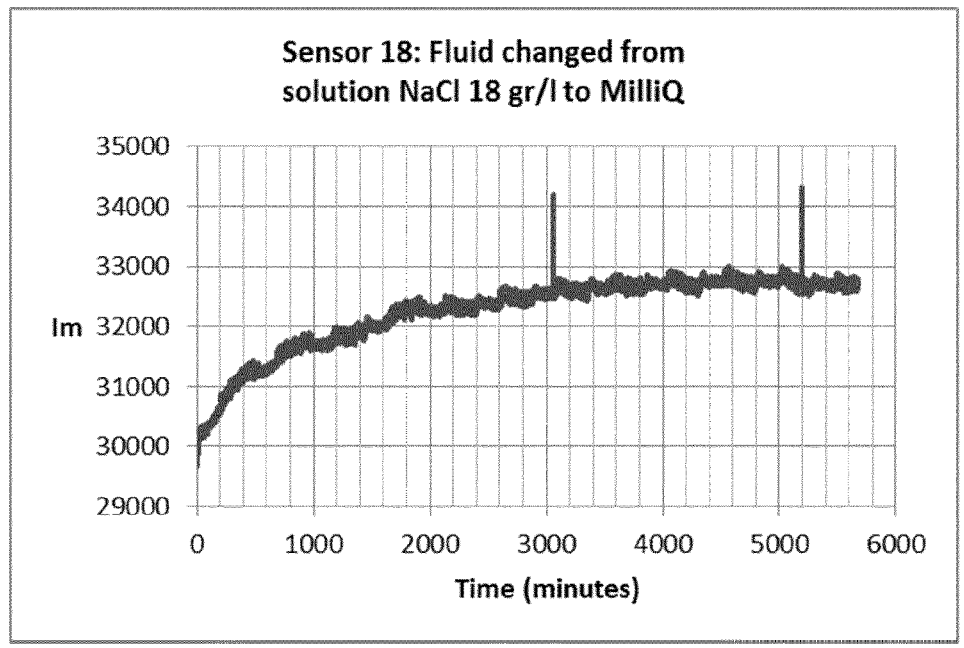
FIG. 7 shows Imaginary (FIG. 7A) and corrected Real part (FIG. 7B) of the luminescence.
Figure 7B:
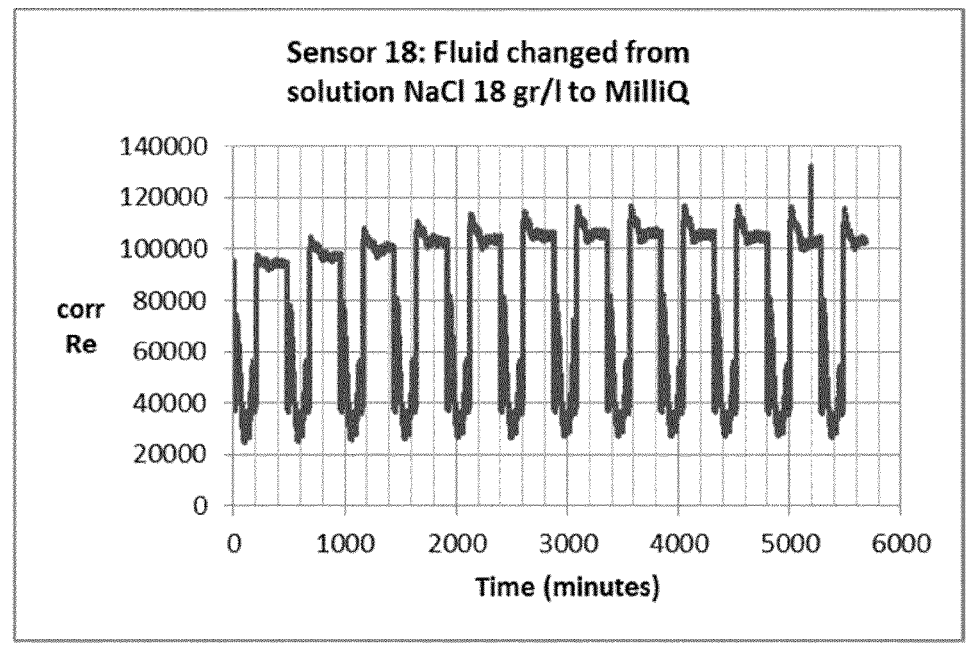

Here k is a constant, reflecting the ratio of sensitivity for osmolarity of the two dyes. The result is shown in FIG. 7 providing in FIG. 7A the Imaginary part of the fluorescence and in FIG. 7B the corrected Real part of the fluorescence.

Figure 8:
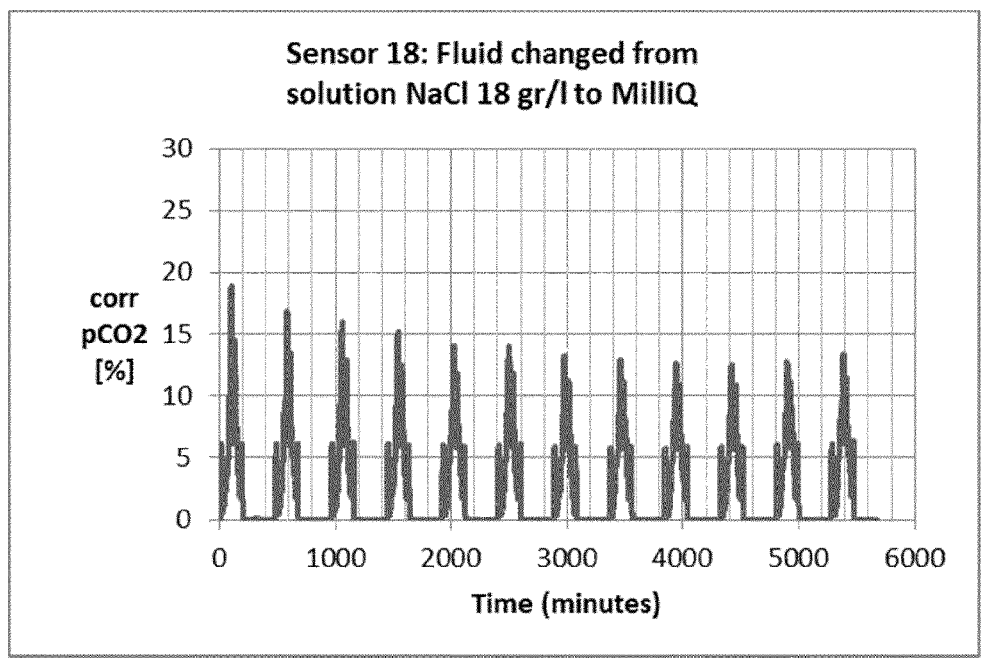
FIG. 8 depicts Imaginary and corrected Real part of the luminescence after correction. The clinical relevant $CO_2$ levels between 0 and 20% are relatively constant over time.

Subsequently, the $CO_2$ fraction was calculated on the basis of Re'(t) and Im(t). The Imaginary and corrected Real part of the fluorescence after correction are shown in FIG. 8. It is noted that the clinical relevant $CO_2$ levels between 0 and 20% are relatively constant over time.

Example 5

Extraction of Response from Reference Dye

The response from the reference dye in Example 2 was extracted from the fluorescence by vector de-composition (see also FIG. 5) according to $$\vec{F} = A\, e^{i\phi} = Re(\vec{F}) + i\, Im(\vec{F}) = A\cos(\omega t) + i\, A\sin(\omega t) = \alpha + i\beta$$

Figure 9B:
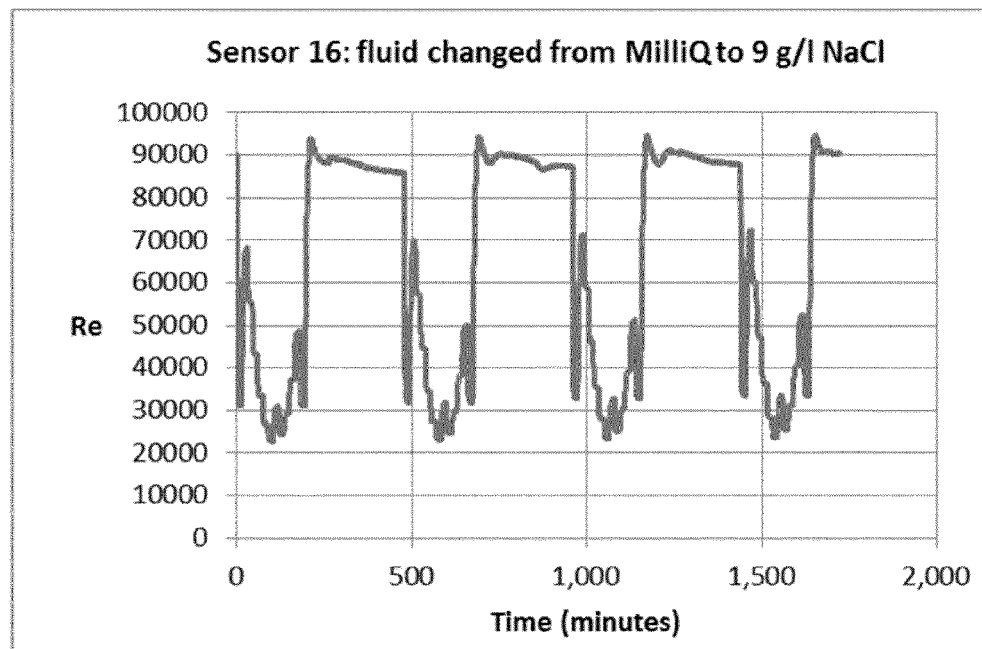

The Imaginary part was insensitive for the applied $CO_2$ modulation and shows an exponential-like decrease (see also FIG. 9 A).

Example 6

Compensation of Sensor Response

In a next step the sensor response of Example 2 was compensated on basis of the reference dye. First, the relative change $\partial(t)$ of the imaginary part (representing the reference dye) was calculated according to:

$$\partial(t) = \frac{\beta(t) - \beta(0)}{\beta(0)}$$

This value was used to correct the Real part according to:

$$k\partial(t) = \frac{\alpha(t) - \alpha'(t)}{\alpha'(t)} \Longrightarrow \alpha'(t) = \frac{\alpha(t)}{1 + k\partial(t)}$$

Here k is a constant, reflecting the ratio of sensitivity for osmolarity of the two dyes. Subsequently, the $CO_2$ fraction was calculated on basis of $\alpha'(t)$ and $\beta(t)$.

Alternatively at least one calibration parameter is adapted by $\partial(t)$. A preferred candidate is x0, which reflects the chemical balance in the sensor.

Figure 10:
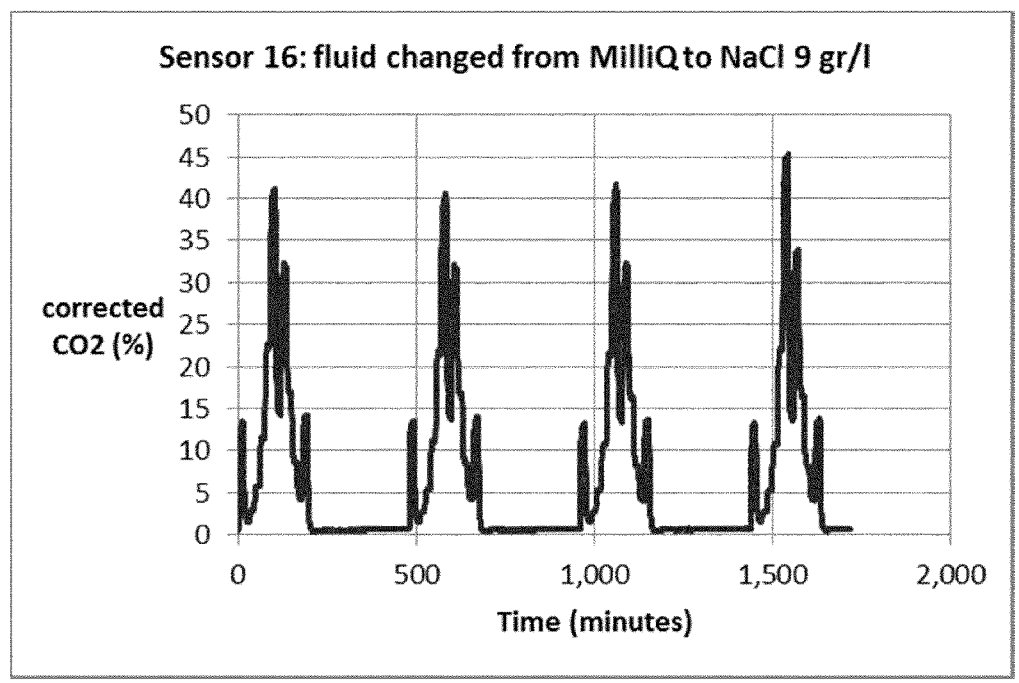
FIG. 10 depicts a corrected sensor response after transfer into a higher osmotic environment according to the present invention. The clinical relevant $CO_2$ levels between 0 and 20% are relatively constant over time.

The corrected sensor response after transfer into a higher osmotic environment as carried out in Example 2 is shown in FIG. 10. It is noted that the clinical relevant $CO_2$ levels between 0 and 20% are relatively constant over time.

The invention claimed is:

1. A method for optically determining concentration of a gas, the method comprising:
 contacting a gas with a reference dye and an indicator dye, the reference dye being in-sensitive to the concentration of the gas with respect to a luminescence response and the indicator dye being sensitive to the concentration of the gas with respect to the luminescence response,
 measuring the luminescence decay times of the reference dye and the indicator dye when in contact with the gas;

measuring a resultant phase angle of the decay times, the resultant phase angle being indicative of the concentration of the gas measuring a luminescent amplitude of the reference dye at a first moment in time; and correcting a measurement of luminescence response of the indicator dye at a second moment in time based on the measured luminescent amplitude of the reference dye at the first moment in time.

2. The method of claim 1, wherein the dyes are excited by a single light source.

3. The method of claim 1, wherein the dyes are excited simultaneously.

4. The method of claim 1, wherein the dyes are provided in a sensing layer of a chemo-optical sensor unit.

5. The method of claim 4, wherein the chemo-optical sensor unit comprises, adjacent to the sensing layer, at least one gas-permeable layer, and wherein the method futher comprises:

passing the gas through the gas-permeable layer prior to the sensing layer.

6. The method of claim 5, further comprising preventing by the gas-permeable layer, light from passing through the gas-permeable layer.

7. The method of claim 5, further comprising disposing a contact medium at least between the gas-permeable layer and a surface layer on which the chemo-optical sensor is to be applied.

8. The method of claim 1, comprising:

measuring a phase behavior of luminescent responses of the reference and indicator dyes by a single detector;

obtaining a luminescent response vector $\vec{F}$ based on the measured phase behavior responses, wherein the luminescence response vector $\vec{F}$ is independent of a total intensity of both luminescent dyes;

de-composing the measured luminescent response vector $\vec{F}$ into an imaginary part ($\beta$) of vector $\vec{F}$ and a real part ($\alpha$) of vector $\vec{F}$, wherein the imaginary part ($\beta$) reflects the reference dye and the real part ($\alpha$) is a summation of a real part of the reference dye and of the indicator dye according to a formula (I), wherein A is an amplitude of the luminescent response vector $\vec{F}$, $i\phi$ is an imaginary phase shift w(t) is frequency of a light modulation, and Re($\vec{F}$) and Im($\vec{F}$) are real and imaginary parts of the luminescent response vector $\vec{F}$ respectively, and wherein formula (I) comprises:

$$\vec{F} = A\ e^{i\phi} = Re(\vec{F}) + i\ Im(\vec{F}) = A\ \cos(\omega t) + i\ A\ \sin(\omega t) = \alpha + i\beta$$

compensating the measured luminescent response of the indicator dye after a first moment in time based on the reference dye according to a formula (II), wherein formula (II) comprises:

$$\alpha' = \frac{\alpha}{1 + k\partial(t)}$$

wherein $$\partial(t) = \frac{\beta(t) - \beta(0)}{\beta(0)}$$

wherein k is a constant reflecting a ratio of sensitivity for osmolarity of said luminescent dyes; and determining the concentration of the gas via the phase angle $\phi$ of the resultant luminescent response vector $\vec{F}$ according to a formula (III), wherein formula (III) comprises:

$$\vec{F} = \alpha' + i\beta.$$

9. The method of claim 8, wherein the imaginary part ($\beta$) and the real part ($\alpha$) are low pass filtered.

10. The method of claim 1, further comprising calibrating the responses of the dyes in one or more different osmotic environments based on a ratio between the luminescence of the reference dye and of the indicator dye in one osmotic environment.

11. The method of claim 1, wherein a ratio between the luminescence of the reference dye and of the indicator dye in one osmotic environment is used as calibrator for changing osmotic environments.

12. A method for quality assessment of measurement of a chemo-optical sensor used for determining the concentration of a gas, the method comprising:

optically determining concentration of a gas according to claim 1;

measuring phase behavior of luminescent responses of reference and indicator dyes by a single detector;

obtaining a luminescent response vector $\vec{F}$ based on the measured phase behavior responses, wherein the luminescent response vector $\vec{F}$ is independent of a total intensity of both luminescent dyes;

de-composing the measured luminescent response vector $\vec{F}$ into an imaginary part ($\beta$) of vector $\vec{F}$ and a real part ($\alpha$) of vector $\vec{F}$, wherein the imaginary part ($\beta$) reflects the reference dye and the real part ($\alpha$) is a summation of the real part of the reference dye and of the indicator dye according to a formula (I), wherein A is an amplitude of the luminescent response vector $\vec{F}$, $i\phi$ is an imaginary phase shift, w(t) is frequency of a light modulation, Re($\vec{F}$) and Im($\vec{F}$) are the real and imaginary parts of the luminescent response vector $\vec{F}$ respectively, wherein formula (I) comprises:

$$\vec{F} = A\ e^{i\phi} = Re(\vec{F}) + i\ Im(\vec{F}) = A\ \cos(\omega t) + i\ A\ \sin(\omega t) = \alpha + i\beta$$

and wherein, a variation of the imaginary part according to formula (I) measured in a time scale longer than 1 hour is indicative of an acceptable measurement quality, and a variation of the imaginary part according to formula (I) measured in a time scale shorter than 1 hour is indicative of a non-acceptable measurement quality.

13. The method of claim 1, wherein said gas concentration is blood gas concentration.

14. The method of claim 1, wherein the gas concentration is determined in an osmotically unbalanced environment.

15. The method of claim 1, wherein the determination of the concentration of the gas is a transcutaneous determination of the concentration of $CO_2$ at a human skin.

* * * * *